US00PP17760P3

(12) United States Plant Patent
Warren et al.

(10) Patent No.: US PP17,760 P3
(45) Date of Patent: May 22, 2007

(54) CALLA LILY PLANT NAMED 'PURPLE HEART'

(50) Latin Name: ***Zantedeschia* spp.**
Varietal Denomination: Purple Heart

(75) Inventors: Andrew G. F. Warren, Tauranga (NZ); Jacobus P. Spaans, Tauranga (NZ)

(73) Assignee: Bloomz Ltd, Tauranga (NZ)

( * ) Notice: Subject to any disclaimer, the term of this patent is extended or adjusted under 35 U.S.C. 154(b) by 63 days.

(21) Appl. No.: 11/183,733

(22) Filed: Jul. 13, 2005

(65) Prior Publication Data

US 2007/0016993 P1 Jan. 18, 2007

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—June Hwu
(74) *Attorney, Agent, or Firm*—Jondle & Associates, P.C.

(57) ABSTRACT

A calla lily plant particularly distinguished by its purple-black flower color, higher flower count, and leaves with white maculation is described.

3 Drawing Sheets

Genus and species: *Zantedeschia* spp.
Variety denomination: 'Purple Heart'.

BACKGROUND OF THE NEW PLANT

The present invention comprises a new and distinct cultivar of calla lily, botanically known as *Zantedeschia* spp., and hereinafter referred to by the cultivar name 'Purple Heart'. The new cultivar was asexually reproduced from vegetative cuttings and tissue culture resulting from the cross of the female parent 'Purple Seedling' (unpatented) and the male parent, 'Pacific Pink' (unpatented).

'Purple Heart' is a product of a planned breeding program intended to create new calla lily plants with purple spathes.

The new cultivar was created in Tauranga, New Zealand and has been asexually reproduced repeatedly by tissue culture in New Zealand. The present invention has been found to retain its distinctive characteristics through successive propagations.

DESCRIPTION OF PHOTOGRAPHS

This new calla lily plant is illustrated by the accompanying photographs which show the blooms and foliage of the plant. The colors shown are as true as can be reasonably obtained by conventional photographic procedures.

DESCRIPTION OF THE NEW CULTIVAR

Figure 1:
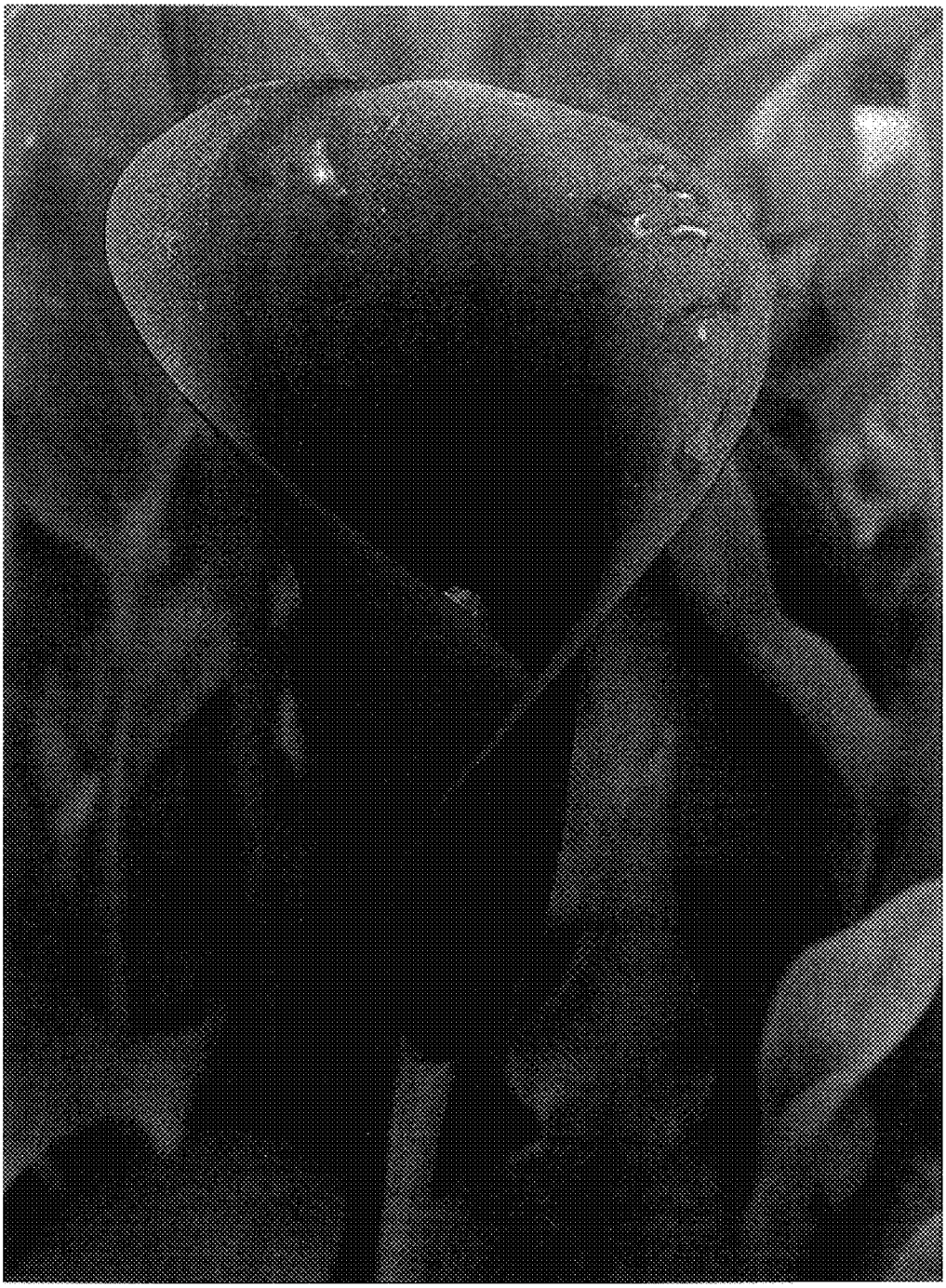
FIG. 1 shows the mature inflorescence.
Figure 2:
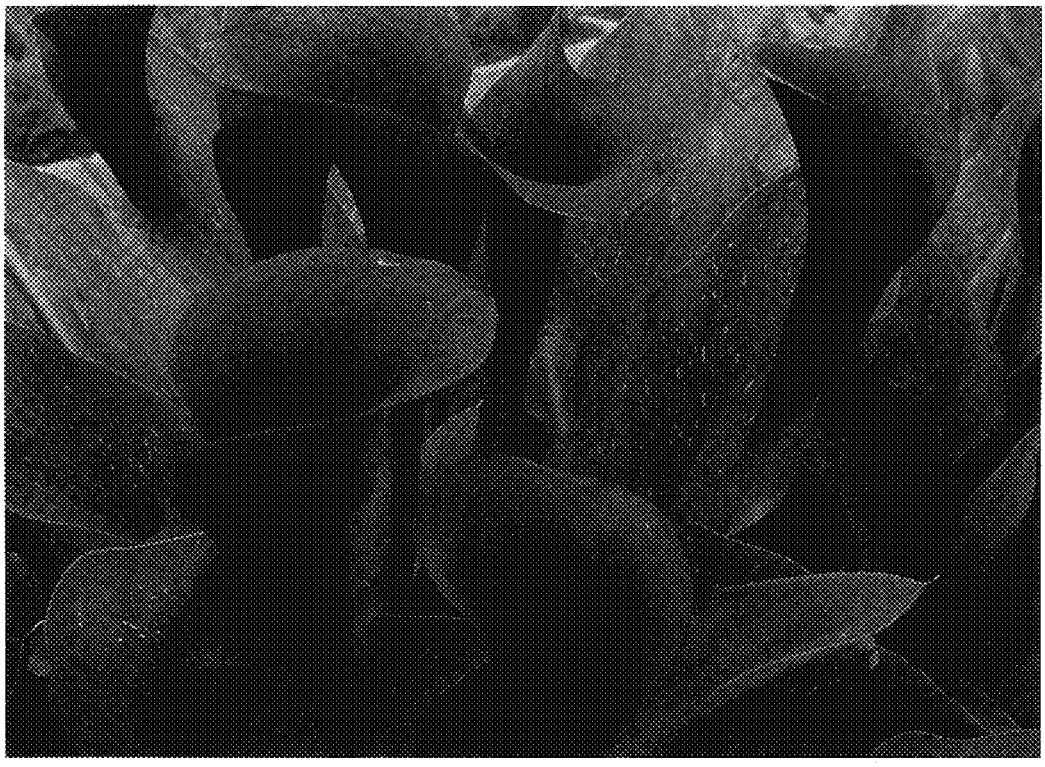
FIG. 2 shows the overall plant habit.
Figure 3:
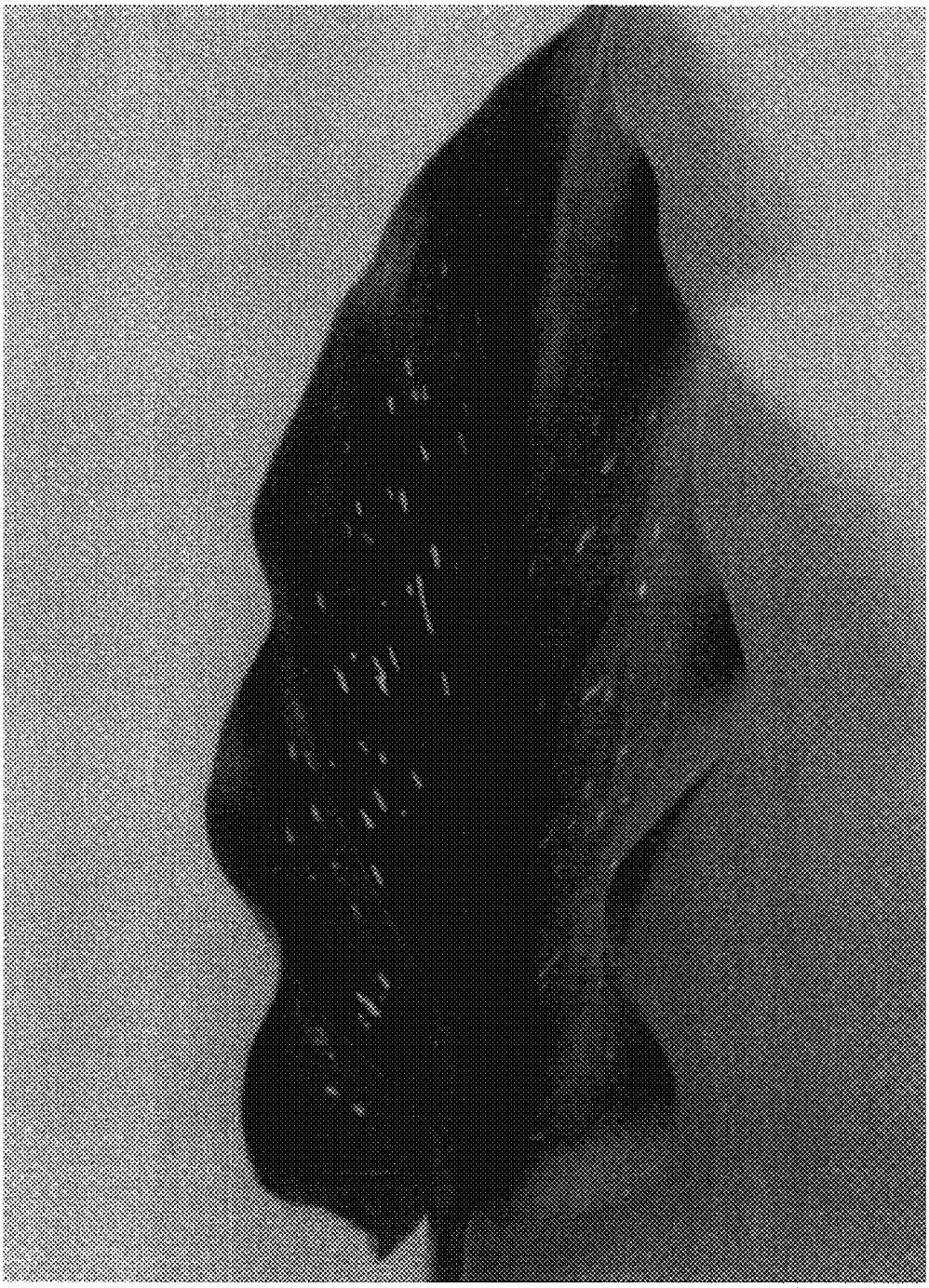
FIG. 3 shows a close-up of the leaf.

The following detailed descriptions set forth the distinctive characteristics of 'Purple Heart'. The data that define these characteristics were collected from asexual reproductions carried out in New Zealand. The plant history was taken on two-year-old plants based on a 3 cm diameter tuber under New Zealand summer conditions. Color references are primarily to The R.H.S. Colour Chart of The Royal Horticultural Society of London (R.H.S.).

DETAILED BOTANICAL DESCRIPTION

Classification:
- *Botanical name.*—*Zantedeschia* spp.
- *Common name.*—Calla lily.

Size:
- *Form.*—Erect.
- *Height of the leaf canopy above the soil.*—45–60 cm.
- *Height of top of inflorescence above the soil.*—50–60 cm.
- *Diameter.*—25–40 cm.
- *Number of inflorescences per tuber size.*—Tuber diameter 3 cm: 1–3. Tube diameter 4 cm: 2–5. Tube diameter 5 cm: 4+.

Leaves:
- *Size.*—Width: 7–12 cm. Length: 18–25 cm.
- *Shape.*—Ovate.
- *Color.*—Upper surface: RHS 137B. Lower surface: RHS 137C.
- *Maculation* (*leaf spots*).—General: Maculation is only on the upper surface of the leaf but is visible from the lower surface. Density: Medium. Color: RHS 155C.
- *Apex.*—Acute to apiculate.
- *Margin.*—Moderately wavy.
- *Margin color.*—RHS 144A (yellow-green).
- *Veins.*—Pinnate.
- *Surface texture.*—Leathery.

Petiole:
- *Average number.*—1 to 3.
- *Length.*—20–25 cm.
- *Diameter.*—0.6–0.8 cm.
- *Color.*—Lower portion: RHS 144B. Upper portion: RHS 144A. Base: RHS 155D.
- *Texture.*—Smooth.
- *Character.*—Strong.

*Sheath.*—Width: 0.6 cm to 0.8 cm. Length: 4 cm to 6 cm. Color: RHS 144A (green).

Roots:

*Color.*—RHS 155 D (white).

*Branching.*—Not branched, attached to the top of the tuber at the apices.

Inflorescence:

*Time to produce a finished flowering plant.*—6–10 weeks depending on climate and environment.

*Lastingness of flowers.*—2–3 weeks.

*Fragrance.*—None.

Flower description:

*Spathe* (*flower body*).—Size: Height: 8–11 cm. Width: 4–6 cm. Color: Upper surface: RHS 59A to RHS 187A. Lower surface: RHS 187A. Veins: Color: RHS 202A (black-purple). Shape: Fluted. Texture: Smooth. Shape: Cup-shaped. Apex: Caudate. Base: Attenuate. Margin: Entire.

*Spadix* (*reproductive organs*).—Size: Length: 2–2.5 cm. Diameter: 0.4–0.7 cm. Color: Base: RHS 187A. Upper: RHS 187A. Position relative to spathe: Upright. Shape: Elongated. Apex: Rounded.

*Peduncle* (*flower stem*).—Length: 35–55 cm. Diameter: 0.5–0.8 cm. Color: Base: RHS 144B. Upper: RHS 144A. Texture: Smooth. Strength: Strong.

Reproductive organs:

*Location of female organs.*—Basal position of the spadix.

*Location of male organs.*—Upper position of the spadix.

*Perianth* (*the floral envelope, calyx and corolla*).—Conspicuous.

*Stamens.*—Not visible before pollen release.

*Pollen color.*—White.

*Pistil.*—Number: 20–30 per spadix. Color: RHS 186D.

Fruit:

*General.*—Whole fruit is round and 3.0–3.5 cm wide and 4.0–6.0 cm long; individual berries are 0.5–0.7 cm in circumference.

*Number.*—10–20 berries.

*Color.*—RHS 187A.

Disease and insect resistance:

*Disease resistance.*—No susceptibility noted to date.

*Pest resistance.*—No susceptibility noted to date.

COMPARISON WITH KNOWN CULTIVARS

When 'Purple Heart' is compared with the female parent 'Purple Seedling' (unpatented), the flower shape of 'Purple Heart' is fluted while the flower shape of 'Purple Seedling' is round. Additionally, the leaf shape of 'Purple Heart' is ovate while the leaf shape of 'Purple Seedling' is cordate.

When 'Purple Heart' is compared with the male parent 'Pacific Pink' (unpatented), the flower color of 'Purple Heart' is purple while the flower color of 'Pacific Pink' is pink. The flower shape of 'Purple Heart' is fluted while the flower shape of 'Pacific Pink' is round. Additionally, the leaf shape of 'Purple Heart' is cordate while the leaf shape of 'Pacific Pink' is ovate.

'Purple Heart' differs from the comparison variety 'Blackjack' (U.S. Plant Pat. No. 15,808) in that 'Purple Heart' has a purple spathe, while 'Blackjack' has a dark-purple spathe. Additionally, 'Purple Heart' has a longer peduncle (35 cm to 55 cm in length) than 'Blackjack' (20 cm to 40 cm in length).

I claim:

1. A new and distinct cultivar of calla lily plant as shown and described herein.

* * * * *